United States Patent [19]

Mutai et al.

[11] 4,298,619
[45] Nov. 3, 1981

[54] PRODUCTION OF FOODS AND DRINKS CONTAINING BIFIDOBACTERIA

[75] Inventors: Masahiko Mutai, Higashi Yamato; Mitsuo Mada, Kodaira; Kiyohiro Shimada, Kunitachi, all of Japan

[73] Assignee: Kabushiki Kaisha Yakult Honsha, Tokyo, Japan

[21] Appl. No.: 119,774

[22] Filed: Feb. 8, 1980

[30] Foreign Application Priority Data

Feb. 23, 1979 [JP] Japan ................................ 54-19724

[51] Int. Cl.³ ........................... A23C 9/12; A23L 2/02
[52] U.S. Cl. ...................................... 426/43; 426/44; 426/61; 426/599
[58] Field of Search ...................... 426/34, 42, 43, 44, 426/48, 61, 599

[56] References Cited

U.S. PATENT DOCUMENTS

| | | | |
|---|---|---|---|
| 4,087,559 | 5/1978 | Mutai et al. | 426/43 |
| 4,091,117 | 5/1978 | Mutai et al. | 426/43 |
| 4,187,321 | 2/1980 | Mutai et al. | 426/43 |

FOREIGN PATENT DOCUMENTS 47-37556 9/1972 Japan.
54-32078 10/1979 Japan.

*Primary Examiner*—David M. Naff
*Attorney, Agent, or Firm*—Wenderoth, Lind & Ponack

[57] ABSTRACT

Foods and drinks containing bifidobacteria are produced by inoculating and cultivating bifidobacteria or a mixture of bifidobacteria and lactic acid bacteria in a medium containing α-starch-transformed rice and bifidobacteria-fermentable sugars, and processing the resultant cultivated medium to produce foods and drinks containing bifidobacteria. The α-starch-transformed rice is produced by cooking rice. The medium for cultivating bifidobacteria may contain milk, and cultivating may be carried out under aerobic conditions.

9 Claims, 3 Drawing Figures

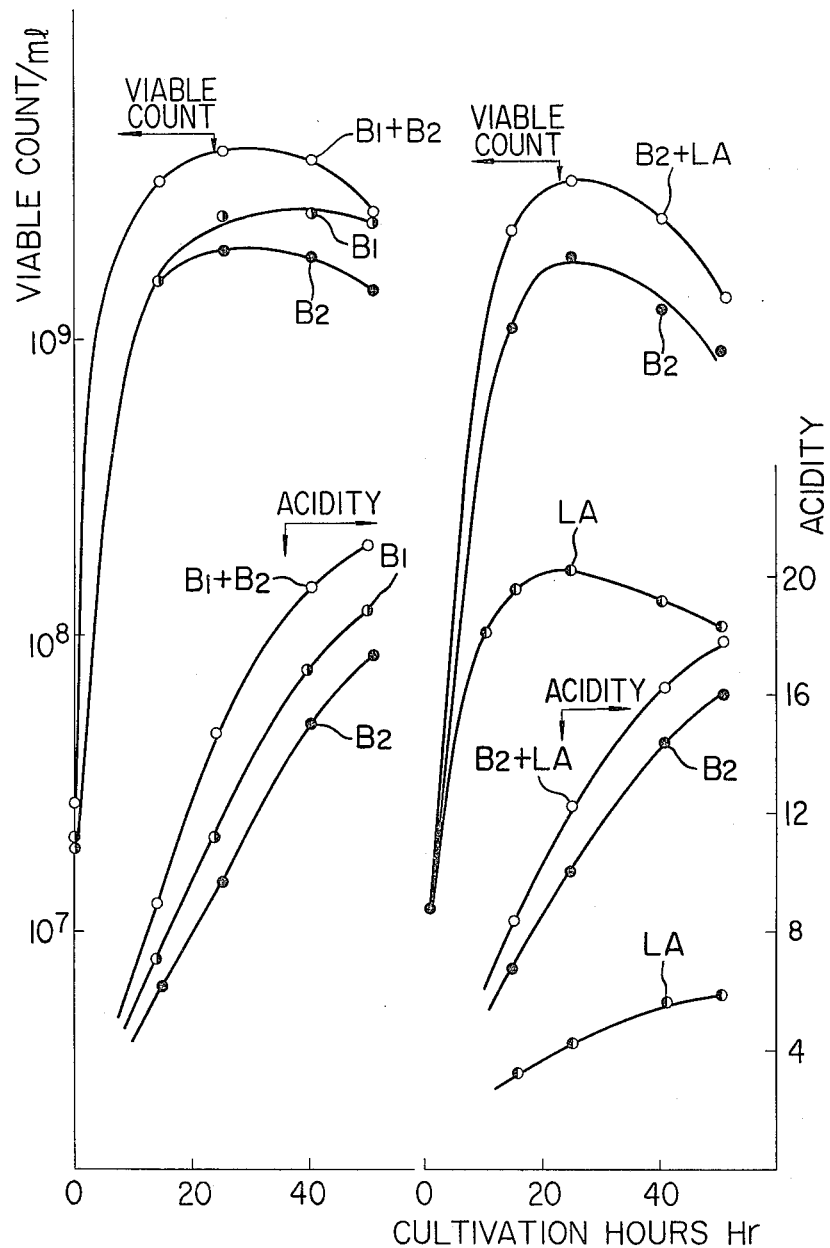

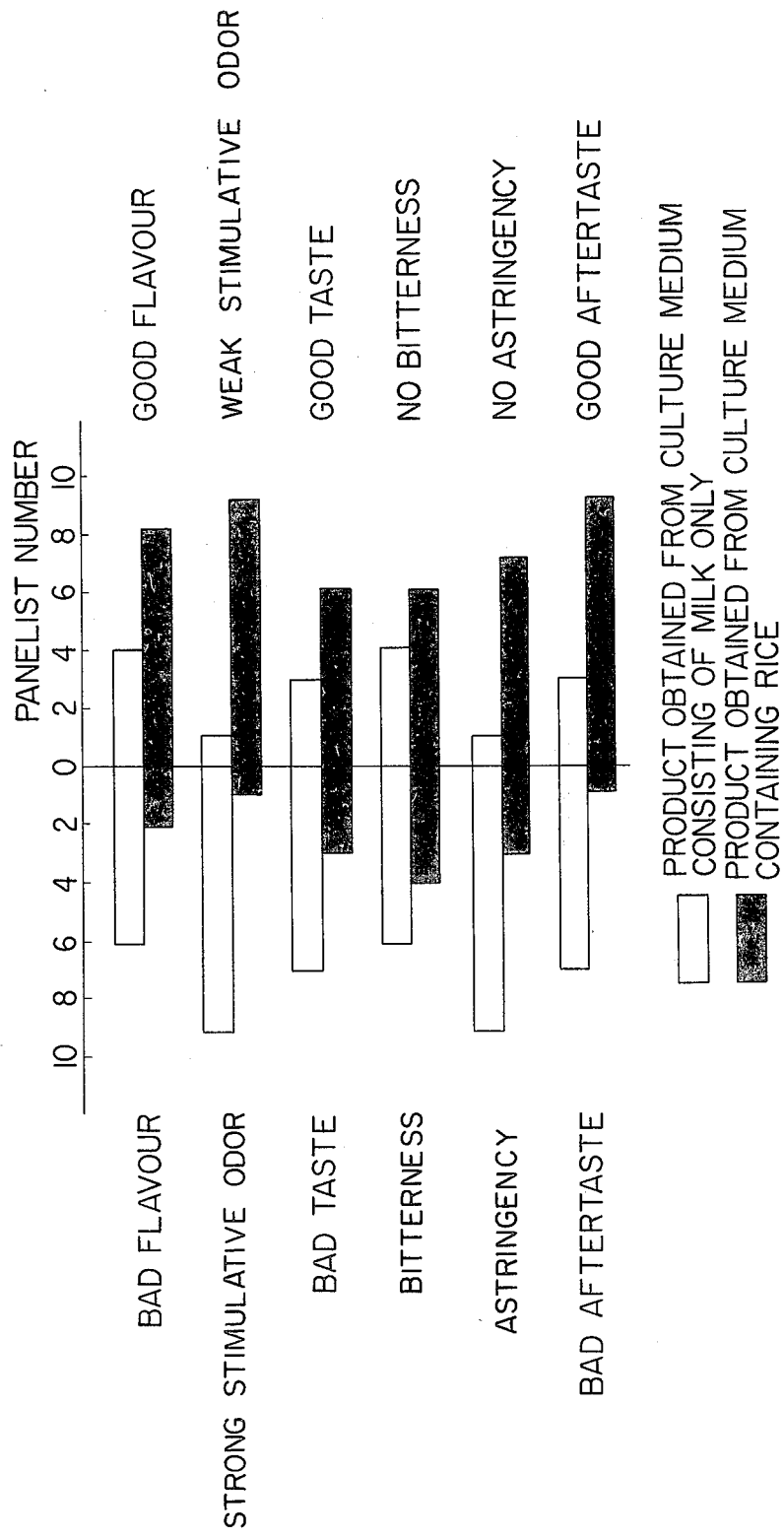

PRODUCTION OF FOODS AND DRINKS CONTAINING BIFIDOBACTERIA

BACKGROUND OF THE INVENTION

This invention relates to a method for producing foods and drinks containing bifidobacteria.

Bifidobacterium predominates in intestinal bacterial flora of suckling infants, and is being watched with keen interest since it has an influence on the health of breast-fed infants.

There are many reports on the study of the physiological significance of this bacteria, clarifying (1) the inhibitory effect on putrefaction by putrefactive bacteria, (2) the inhibitory effect on production of toxic amines, (3) the digestive effect on human milk casein by the action of phosphoprotein phosphatase, and (4) the effect of suppressing the growth of pathogenic bacteria by lowering intestinal pH following production of organic acids such as lactic acid, acetic acid, and formic acid.

However, this Bifidobacterium favourable to infants is present in a very small amount in the intestines of bottle-fed infants, which is considered to be one of the causes for their susceptibility to intestinal diseases, greater than that of breast-fed infants.

Aimed at approximating the intestinal flora of bottle-fed infants to that of breast-fed infants, an attempt has been made to produce Bifidobacterium-containing powdered milk for infants and to modify powdered milk for infants in such a manner as to be similar to a mother's milk.

However, due to the problems as mentioned below, it has been difficult to practice an industrial cultivation of Bifidobacterium in a medium consisting of milk only.

That is, as compared with dairy lactic acid bacteria which are widely used in processing milk, Bifidobacterium has the following problems:

(1) An industrial mass cultivation is difficult since Bifidobacterium requires strict anaerobic conditions for growth, and accordingly entails a large equipment cost and requires high level cultivation techniques;

(2) The nutritional requirement for the cultivation is complicated and fastidious and therefore the bacteria do not substantially propagate on a pure cow's milk medium containing no growth promoting substance such as yeast extract, peptone and the like; and (3) Acetic acid, the main metabolic product of Bifidobacterium, is highly stimulative, and therefore generally impairs the taste and flavour of foods and drinks containing the same.

We have found that bifidobacteria having the above mentioned properties can be prosperously propagated under the same aerobic culture conditions as in the cultivation of dairy lactic acid bacteria in a medium containing as the main component a pasty or milky product of α-starch-transformed non-glutinous or glutinous rices, polished, whole, non-polished or powdered thereof, and further containing sugars fermentable by Bifidobacterium, such as glucose, lactose, fructose, galactose and the like (the sugar may vary depending on the species of Bifidobacterium used), and that the cultivated product has a good flavour since the fermentation product, acetic acid, well matches with the flavour of cooked rice.

SUMMARY OF THE INVENTION

An object of this invention is to provide a method for producing foods and drinks containing bifidobacteria, characterized by inoculating and cultivating bifidobacteria or bifidobacteria and lactic acid bacteria in a medium comprising a milky mixture containing rice treated for α-starch transformation and sugars fermentable by bifidobacteria or further containing milk components in addition to the above ingredients, and optionally processing the cultivated product into a form suitable for foods and drinks.

BRIEF DESCRIPTION OF THE DRAWINGS

FIGS. 1 and 2 show graphs illustrating the state of cultivation with the passage of the cultivation time.

FIG. 3 shows the results of the organoleptic evaluation of a product cultivated with bifidobacteria.

DETAILED EXPLANATION OF THE INVENTION

The above mentioned properties of bifidobacteria are illustrated by the following experiments. Viable cell count expressed by count per ml was measured in accordance with the method described in "J. Food Hyg. Soc. Japan" (Vol. 18, pp. 537–546, 1977). Titratable acidity was expressed by amount in ml of 0.1 N NaOH solution required to neutralize 10 ml of sample.

Experiment 1

A culture medium for this Experiment was prepared by adding about 750 ml of water to 150 g each of washed unpolished-, whole-, and polished- non-glutinous rices, heating each mixture at 120° C. for 15 minutes, emulsifying it by a mixer, adding 30 g of lactose to it and finally topping up to 1000 ml by the addition of water. A reconstituted skim milk having a non-fat milk solid concentration of 15% was used as a reference culture medium.

Each culture medium thus prepared was placed in a 2000 ml-conical flask having a cotton plug, and was then sterilized at 120° C. for 20 minutes. After cooling, 3.0% of each starter of bifidobacteria previously prepared was inoculated in the respective medium, and was subjected to a static culture at 37° C. for 24 hours. Acidity and viable cell count were then measured, and the results are shown in Table 1.

TABLE 1

| Bifido-bacteria | unpolished rice + lactose | | whole rice + lactose | | polished rice + lactose | | milk | |
|---|---|---|---|---|---|---|---|---|
| | acidity | viable count | acidity | viable count | acidity | viable count | acidity | viable count |
| B. bifidum YIT4005 | 8.3 | $6.8 \times 10^8$ | 8.1 | $6.6 \times 10^8$ | 7.2 | $5.6 \times 10^8$ | 6.3 | $4.2 \times 10^8$ |
| B.bifidum E | 7.2 | $5.0 \times 10^8$ | 7.0 | $5.5 \times 10^8$ | 6.8 | $4.2 \times 10^8$ | 2.3 | $5.8 \times 10^5$ |
| B.breve Y | 9.6 | $7.9 \times 10^8$ | 9.4 | $7.1 \times 10^8$ | 8.3 | $6.9 \times 10^8$ | 3.3 | $3.1 \times 10^5$ |
| B.breve S | 9.0 | $6.6 \times 10^8$ | 9.1 | $6.3 \times 10^8$ | 8.5 | $5.6 \times 10^8$ | 2.5 | $4.2 \times 10^4$ |
| B.longum | 5.8 | $4.1 \times 10^8$ | 5.6 | $4.3 \times 10^8$ | 5.0 | $4.0 \times 10^8$ | 2.8 | $2.0 \times 10^4$ |

TABLE 1-continued

| Bifido-bacteria | Media | | | | | | | |
|---|---|---|---|---|---|---|---|---|
| | unpolished rice + lactose | | whole rice + lactose | | polished rice + lactose | | milk | |
| | acidity | viable count | acidity | viable count | acidity | viable count | acidity | viable count |
| ATCC-15707 B.adolescentis | 5.5 | $3.9 \times 10^8$ | 5.0 | $3.6 \times 10^8$ | 4.4 | $2.5 \times 10^8$ | 2.5 | $3.8 \times 10^4$ |
| B.infantis | 4.8 | $1.4 \times 10^8$ | 4.6 | $1.5 \times 10^8$ | 3.8 | $8.9 \times 10^7$ | 2.6 | $5.9 \times 10^4$ |

Note:
Starting Viable Cell Count: $8.5 \times 10^5 \sim 1.3 \times 10^7$, Acidity: $1.3 \sim 1.5$ In the reference milk medium, strains other than B. bifidum YIT 4005 (a mutant of bifidobacteria having properties of propagating under aerobic conditions in a milk medium Deposit No. FERM-3372 at Fermentation Research Institute, Government Industrial Research, Ministry of International Trade and Industry) were not totally propagated. On the other hand, in the respective milky culture medium containing rice as the starting material, all the bifidobacteria were vigorously propagated.

According to other experiments wherein the concentration of cuture medium was varied, it was proved that propagation was accelerated in proportion to the increase in the concentration of rice until the concentration of rice reached 20%. If the concentration exceeds the above value, starching occurs and accordingly amylase treatment is required. However, this treatment did not have a substantial influence on the propagation.

With regard to unpolished-, whole-, and polished-glutinous rices, substantially the same results as in the above were obtained.

Experiment 2

The same procedures as in Experiment 1 were repeated, except that a medium used for this experiment was prepared by cooking unpolished-, whole-, and polished-non-glutinous rices, emulsifying it at a concentration of 15%, and adding to the emulsion 2.0% of lactose and 1.0-15% of skim milk powder.

Table 2 shows the results obtained with media containing skim milk powder at a concentration of 5%. In the media containing milk components in addition to rice and sugar, the propagation of bifidobacteria was accelerated as compared with Experiment 1 wherein milk component was not used. The effect of the milk components on accelerating propagation was enhanced in proportion to the increase in the concentration of skim milk powder until the concentration reached 10%. If the concentration exceeded the above value, no further enhancement of the effect on accelerating propagation was achieved.

Substantially the same results are to be obtained by the use of whey powder.

TABLE 2

| Bifido-bacteria | rice | | | | | |
|---|---|---|---|---|---|---|
| | unpolished rice | | whole rice | | polished rice | |
| | acidity | viable count | acidity | viable count | acidity | viable count |
| B.bifidum YIT 4005 | 13.5 | $6.2 \times 10^9$ | 13.3 | $6.0 \times 10^9$ | 12.6 | $5.8 \times 10^9$ |
| B.bifidum E | 9.5 | $7.6 \times 10^8$ | 9.6 | $7.0 \times 10^8$ | 9.4 | $6.8 \times 10^8$ |
| B.breve Y | 11.8 | $5.0 \times 10^9$ | 10.7 | $3.3 \times 10^9$ | 10.1 | $3.4 \times 10^9$ |
| B.breve S | 10.0 | $9.0 \times 10^8$ | 9.0 | $8.2 \times 10^8$ | 9.1 | $7.8 \times 10^8$ |
| B.longum ATCC-15707 | 7.9 | $6.7 \times 10^8$ | 7.6 | $5.8 \times 10^8$ | 7.2 | $5.3 \times 10^8$ |
| B.adolescentis | 6.5 | $5.1 \times 10^8$ | 6.3 | $5.0 \times 10^8$ | 6.0 | $4.1 \times 10^8$ |
| B.infantis | 6.6 | $4.9 \times 10^8$ | 6.0 | $4.1 \times 10^8$ | 5.6 | $3.9 \times 10^8$ |

Note:
Starting Viable Cell Count: $1.0 \sim 3.4 \times 10^7$, Acidity: $1.7 \sim 2.0$

Experiment 3

Two species of bifidobacteria or a mixture of bifidobacteria and lactic acid bacteria were inoculated in a milky medium prepared in such a manner as to contain 15% of unpolished non-glutinous rice, 5% of skim milk powder and 2% of lactose, and was subjected to a static culture at 37° C. The inoculum of the starter of each strain was respectively 2%. FIGS. 1 and 2 show the results of the acidity and viable cell counts measured with the passage of time during cultivation in comparison with the results obtained by single cutivation of each strain. The strains used in this Experiment are as follows:

$B_1$: B. bifidum YIT 4005
$B_2$: B. breve Y
LA: Lactobacillus acidophilus

As can be seen from the two Figures, a certain species of strain was vigorously propagated in a rice-containing medium when subjected to a mixed cultivation.

Experiment 4

B. bifidum YIT 4005 was inoculated in a medium containing 15% of whole rice, 5% of skim milk powder and 2.0% of lactose and in a skim milk medium having a non-fat milk solid concentration of 15%, and was cultivated at 37° C. for 24 hours. With regard to the culture thus obtained, organoleptic evaluation was made by a panel consisting of 10 trained panelists. The results are shown in FIG. 3.

Both cultures had almost equal values each other with regard to acidity and ratio of acetic acid/lactic acid (see Table 3). However, culture of the rice-containing medium was evaluated to have a better flavour since the flavour of cooked rice well matches with acetic acid and the stimulative smell of acetic acid is weaker as compared with the product cultivated in the milk-containing medium.

TABLE 3

| Medium | Culture Acidity | Acetic Acid/ Lactic Acid |
|---|---|---|
| medium consisting of milk only | 6.8 | 1.75 |
| medium containing rice | 7.5 | 1.80 |

The present invention was accomplished in view of the above knowledge. Thus, the present invention resides in a method for producing foods and drinks containing bifidobacteria, characterized by inoculating and cultivating bifidobacteria or bifidobacteria and lactic acid bacteria in a medium comprising a milky mixture containing rice treated for α-starch transformation and sugars fermentable by bifidobacteria or further containing milk components in addition to the above ingredients, and optionally processing the cultivated product into a form suitable for foods and drinks.

As clearly described above, any glutinous or non-glutinous rice can be used in the method of this invention, and the rice may or may not, be polished or milled, to any degree. When these rices are used in a medium for cultivating bifidobacteria, they are preferably made into a homogenous milky state by the method used in Experiment 1 or a method of grinding and heating in water. An appropriate concentration of rice in a medium is 10-20%, preferably 15%.

Sugars such as lactose, fructose and glucose are the most preferable bifidobacteria-fermentable sugars since they are easily available and fermentable by all of the bifidobacteria. It is not necessary to use pure sugars, but any edible material containing these fermentable sugars, for example, lactose-containing milk, skim milk, whey and the like can be used as a medium component. Milk components are particularly preferable since they accelerate the propagation of bifidobacteria and provide a product having a good nutrition balance. A part or the whole part of the rice may be previously treated with amylase or with amylase-producing *Aspergillus oryzae, Aspergillus niger, Bacillus subtilis* and the like to produce glucose in an amount sufficient for the propagation of bifidobacteria, and the glucose thus produced may be used as a fermentable sugar for bifidobacteria. This method has advantages in that the emulsification of rice proceeds along with saccharification, and that a unique flavour can be obtained.

The concentration of bifidobacteria-fermentable sugars in a medium should preferably be 1-5%, more preferably about 3%.

Any cultivation suppliments or seasonings, spices, nutritions and the like may be added to a medium in addition to the above components.

Bifidobacteria to be inoculated in the above mentioned homogenous milky medium are not specially limited, and 2 species or more of bifidobacteria may be used. In combination with bifidobacteria, Lactic acid bacteria may be inoculated, preferable examples of which include *Lactobacillus acidophilus, L. casei, L. bulgaricus, Streptococcus thermophilus* and the like.

The cultivation of bifidobacteria can be carried out under aerobic conditions in the same manner as in the cultivation of ordinary lactic acid bacteria, and strictly anaerobic conditions are not required. This is a great advantage of this invention, and the conventional apparatus and techniques used in the cultivation of lactic acid bacteria can be used as they are.

Under normal cultivation conditions, viable cell count reaches maximum after 18-24 hour cultivation, and pH is gradually decreased because acid is formed along with the passage of the cultivation time. The production of acetic acid by bifidobacteria starts at the initiation of cultivation. If the cultivation is further continued, viable cell count starts to be decreased after 24 hours and the production of acid is continued for some time but the production of acid stops to some extent. Thus, taking the use of the cultivated product into consideration, cultivation is stopped when the pH of the medium reaches 4.2 to 5.6. In most cases using bifidobacteria per se, the viable cell count of bifidobacteria should preferably be more than $10^7$ per ml. According to the culture method of this invention, it is quite easy to obtain a viable cell count of $10^{8-9}$/ml.

The product of this invention contains acetic acid 80-120 mM/l and lactic acid 50-70 mM/l as the main metabolites in addition to the viable bifidobacteria. The contents of these acids are not specially different from those in conventional bifidobacteria culture, but the acetic acid well matches with emulsified rice and therefore the cultivated product of this invention deserves much higher organoleptic evaluation than the conventional cultivated products. Thus, the cultivated product of this invention can be served, as it is, or as a food containing viable bifidobacteria without flavouring. The product of this invention may be served as a drink by optionally adding sweetening materials, fruit juice, water, spices or the like to modulate the concentration and flavour. The product can also be served as powdery or tablet-like foods or medicinal preparations containing viable bifidobacteria by drying. As long as the bifidobacteria do not perish, any conventional processing techniques and any processed forms can be used.

The present invention is further illustrated by the following Examples.

EXAMPLE 1

To 15 Kg of fully washed polished non-glutinous rice, was added 70 liters of water, and the resultant mixture was heated at 121° C. for 15 minutes. The mixture was then emulsified in a mixer, and the mixture was topped up to 100 liters by the addition of water. To this mixture, was added 2 kg of skim milk powder, and the mixture was sterilized at 121° C. for 40 minutes. The mixture was then cooled to 37° C. while stirring.

Into the milky rice medium thus prepared, 3% by volume of the starter of *B. bifidum* YIT-4005 was inoculated, and was cultivated at 37° C. for 24 hours.

After cultivation, the culture was homogenized in a homogenizer (150 Kg/cm$^2$), and 40 liters of syrup containing 4.8 Kg of sucrose was mixed therewith, thus producing a drink having an acidity of 5.4 and containing bifidobacteria in a count of $4.3 \times 10^8$/ml. The product thus obtained had a less stimulative smell and provided a satisfactory taste and flavour.

EXAMPLE 2

To 15 Kg of thoroughly washed whole glutinous rice, was added 70 liters of water, and the mixture was heated at 121° 1 C. for 15 minutes. In order to facilitate emulsification, 50 g of liquifying amylase (70,000 units/g) was added to the mixture, and the mixture was emulsified in a mixer. To this mixture, 1 Kg of lactose and 10 liters of cow's milk were added, and the mixture was topped up to 100 liters by the addition of water. The mixture was then sterilized at 121° C. for 40 minutes, and was cooled to 37° C. while stirring. Into the medium thus prepared, 5% of the starter of *B. adolescentis* was inoculated, and was cultivated at 37° C. for 40 hours.

After cultivation, the culture was treated in the same manner as in Example 1 to obtain a drink having an acidity of 6.1 and containing viable bifidobacteria in an amount of $8.0 \times 10^7$/ml.

Example 3

To 2 Kg of thoroughly washed polished non-glutinous rice, was added 7 liters of water, and the mixture was heated at 121° C. for 20 minutes. After cooling, 200 g of seed starter of *Aspergillus oryzae* was added to the mixture, and the mixture was shaken at 37° C. for 40 hours to saccharify a part of the rice, thus forming glucose. Thereafter, the mixture was emulsified in a mixer, and was topped up to 10 liters. To the emulsion thus prepared, was added 5 liters of syrup containing 600 g of sucrose and 30 g of gelatin, and the resultant mixture was sterilized. Into the medium thus prepared, 2% each of the starter of *B. breve* Y and *B. longum* (ATCC-15707) was inoculated for culture at 37° C. for 12 hours to obtain a sweetwine flavoured yoghurt-like food. The product thus obtained had an acidity of 5.2, and the viable cell count was $2.2 \times 10^8$/ml for *B. breve* Y and $7.8 \times 10^7$/ml for *B. longum*.

Example 4

One Kg of polished nonglutinous rice was thoroughly washed and dried. The rice was then powdered by a grinder, and 5 liters of water was added to the powdered rice. The mixture was then heated at 121° C. for 15 minutes. After cooling the mixture to 55° C., 2 g of saccharifying amylase (50,000 units/g) was added to the mixture while stirring thoroughly, and the resultant mixture was treated at 55° C. for 1 hour. After the amylase-treatment, the mixture was topped up to 10 liters by the addition of water, and was sterilized. After cooling to 37° C., the mixture was inoculated with the starter of *Saccharomyces sake,* and was cultivated at 30° C. for 20 hours. Thereafter, the culture medium thus prepared was sterilized again, and 2% each of the starter of *B. bifidum* E and *Lactibacillus acidophilus* was inoculated into the medium. The cultivation was carried out at 37° C. for 30 hours.

After cultivation, the culture was homogenized in a homogenizer, and 2 liters of syrup containing 300 g of sucrose was added to the culture. The product thus obtained contained a small amount of alcohol, and had a titrarable acidity of 9.6 and the viable cell count of $1.5 \times 10^8$/ml for bifidobacteria and $6.6 \times 10^7$/ml for lactobacilli.

Example 5

To the culture prepared using the same materials in the same manner as in Example 1, were added 5 Kg of skim milk powder, 5 Kg of sugar and 1 Kg of Vitamin C, and the mixture was dried by a spray drier, thus producing 26.5 Kg of powdery food containing $7.1 \times 10^8$/g of bifidobacteria.

What we claim is:

1. A method of producing foods and drinks containing bifidobacteria by inoculating and cultivating bifidobacteria or a mixture of bifidobacteria and lactic acid bacteria in a medium consisting essentially of 10 to 20 percent by weight α-starch-transformed rice, which rice has been transformed by cooking, and bifidobacteria-fermentable sugars in an amount of 1–5 percent of the total weight of the medium to produce a bifidobacteria-containing medium having a bifidobacteria cell count of at least $10^7$ cells/ml., and preparing a food or drink from said bifidobacteria-containing medium.

2. A method according to claim 1, in which the medium contains two species or more of viable bifidobacteria.

3. A method according to claim 1 wherein said medium further consists essentially of milk in an amount of 1–15 percent by weight.

4. A method according to claim 1 wherein sweetening materials, fruit juices or spices are added to the bifidobacteria-containing medium.

5. A method according to claim 1 wherein said bifidobacteria-fermentable sugar is at least one selected from the group consisting of glucose, lactose, fructose, galactose and mixtures thereof.

6. A method according to claim 1 wherein the bifidobacteria-containing medium is dried to produce a dried product.

7. A method according to claim 1 in which cultivation is stopped when the pH of the medium is between 4.2 to 5.6.

8. A method according to claim 1 in which the cultivation is carried out under aerobic conditions.

9. A food or drink prepared from the bifidobacteria-containing medium produced by the method of claim 1, 2, 3, 4, 5, 6, 7, or 8.

* * * * *